United States Patent
Terry et al.

[11] Patent Number: 5,989,560
[45] Date of Patent: Nov. 23, 1999

[54] HERBAL INTESTINAL TRACT CLEANSER

[75] Inventors: Travis L. Terry, Clearwater; Tommy Stanley Watson; Brenda F. Watson, both of Tarpon Springs, all of Fla.

[73] Assignee: Renew Life, Inc., Tarpon Springs, Fla.

[21] Appl. No.: 09/201,920

[22] Filed: Dec. 1, 1998

Related U.S. Application Data

[60] Provisional application No. 60/067,270, Dec. 3, 1997.

[51] Int. Cl.$^6$ .................................................. A61K 35/78
[52] U.S. Cl. .......................................................... 424/195.1
[58] Field of Search ............................................ 424/195.1

*Primary Examiner*—Jean C. Witz
*Attorney, Agent, or Firm*—Donald R. Fraser

[57] ABSTRACT

An herbal formulation comprises a liquid component and a solid component. The liquid component comprises black walnut, wormwood, clove, orange peel, and marshmallow. The solid component comprises wormwood, black walnut, quassia, clove, pumpkin seed, deodorized garlic, pippli, cascara sagrada, calcium undecylenate, caprylic acid, pau d'arco, rosemary oil, thyme, bismuth citrate, and grapefruit seed.

22 Claims, No Drawings

HERBAL INTESTINAL TRACT CLEANSER

This application claims the benefit of U.S. provisional application Ser. No. 60/067,270 filed Dec. 3, 1997.

FIELD OF THE INVENTION

This invention relates generally to an herbal food supplement and intestinal tract cleanser. More particularly, the invention is directed to an herbal formulation useful for cleansing parasites and candida from the intestinal tract of the human body.

BACKGROUND OF THE INVENTION

Herbal formulations can provide a supplement to the daily human diet, and additionally can provide a natural way to cleanse the intestinal tract of parasites and candida, as well as other toxins and food particles. Such formulations are useful for treating a condition known as "leaky gut."

Leaky gut is a condition in which the mucosa of the intestinal tract is compromised, thereby allowing toxins and food particles to penetrate the lining of the intestinal tract and enter the body's blood stream. The body itself may naturally attempt to counteract this phenomenon, usually with several negative side effects. Firstly, the body may attempt to produce antibodies to combat the toxins. This will result in the body developing allergies to the foods which have caused the breakdown of the intestinal tract lining. Furthermore, the liver may increase its production of detoxifying enzymes. The activation of some of these enzymes may release harmful free radicals as a byproduct. These oxidizing free radicals may, in turn, damage the liver and other tissues, resulting in a weakened immune system.

Symptoms of leaky gut may include irritable bowel disease, chronic fatigue, food allergies, and arthritis.

It would be desirable to prepare an herbal formulation which would act as a food supplement as well as cleanse parasites and candida from the body's intestinal tract, thus allowing rejuvenation of the intestinal tract lining to diminish the passage therethrough of toxins and food particles.

SUMMARY OF THE INVENTION

Accordant with the present invention, there surprisingly has been discovered an herbal formulation which acts as a food supplement, and is useful for cleansing parasites and candida from the intestinal tract. The herbal formulation comprises a liquid and a solid, said liquid comprising:

black walnut;
wormwood;
clove;
orange peel; and
marshmallow; and
said solid comprising:
wormwood;
black walnut;
quassia;
clove;
pumpkin seed;
deodorized garlic;
pippli;
cascara sagrada;
calcium undecylenate;
caprylic acid;
pau d'arco;
rosemary oil;
thyme;
bismuth citrate; and
grapefruit seed.

The herbal formulation of the present invention is useful as a food supplement, and additionally is particularly useful for cleansing parasites and candida from the body's intestinal tract.

DETAILED DESCRIPTION OF THE PREFERRED EMBODIMENTS

The present invention is directed to an herbal formulation useful as a food supplement and for cleansing parasites and candida from the body's intestinal tract. The formulation comprises a liquid and a solid. The liquid comprises black walnut, wormwood, clove, orange peel, and marshmallow. The solid comprises wormwood, black walnut, quassia, clove, pumpkin seed, deodorized garlic, pippli, cascara sagrada, calcium undecylenate, caprylic acid, pau d'arco, rosemary oil, thyme, bismuth citrate, and grapefruit seed. All of the recited ingredients are well-known in the food supplements and nutrition industry.

The liquid component of the herbal formulation is typically dispensed from a dropper bottle, so that the liquid may be placed drop-wise into a drink. The solid component may be compressed and formed into a tablet, which can then be swallowed. The herbal formulation according to the present invention is designed to be taken orally.

Black walnut is present in both the liquid and solid components of the inventive formulation, acting as an antiparasitic agent. The black walnut comprises from about 15 to about 25 weight percent of the liquid component, and from about 7 to about 15 weight percent of the solid component.

Wormwood is present in both the liquid and solid components of the inventive formulation, acting as a digestive aid and broad spectrum antiparasitic. The wormwood comprises from about 15 to about 25 weight percent of the liquid component, and from about 7 to about 15 weight percent of the solid component.

Clove is present in both the liquid and solid components of the inventive formulation, acting as a digestive aid. The clove comprises from about 15 to about 25 weight present of the liquid component, and from about 2 to about 6 weight percent of the solid component.

Orange peel is present in the liquid component of the inventive formulation, acting as a digestive aid. The orange peel comprises from about 15 to about 25 weight percent of the liquid component.

Marshmallow is present in the liquid component of the inventive formulation, acting as an agent for removing mucus from the intestinal tract. The marshmallow comprises from about 15 to about 25 weigh percent of the liquid component.

Quassia is present in the solid component of the inventive formulation, acting as an agent for treating roundworms and ringworms. The quassia comprises from about 7 to about 15 weight percent of the solid component.

Pumpkin seed is present in the solid component of the inventive formulation, acting as an agent for treating pinworms and tapeworms. The pumpkin seed comprises from about 2 to about 6 weight percent of the solid component.

Deodorized garlic is present in the solid component of the inventive formulation, acting as an antifungal and antibacterial agent. The deodorized garlic comprises from about 5 to about 10 weight percent of the solid component.

Pippli is present in the solid component of the inventive formulation, acting as a broad spectrum antiparasitic. The pippli comprises from about 1 to about 2 weight percent of the solid component.

Cascara sagrada is present in the solid component of the inventive formulation, acting as a peristaltic stimulant. The cascara sagrada comprises from about 5 to about 10 weight percent of the solid component.

Calcium undecylenate is present in the solid component of the inventive formulation, acting as an antifungal agent. The calcium undecylenate comprises from about 10 to about 20 weight percent of the solid component.

Caprylic acid is present in the solid component of the inventive formulation, acting as a antifungal agent. The caprylic acid comprises from about 5 to about 10 weight percent of the solid component.

Pau d'arco is present in the solid component of the inventive formulation, acting as an antibacterial agent. The pau d'arco comprises from about 5 to about 10 weight percent of the solid component.

Rosemary oil is present in the solid component of the inventive formulation, acting as a digestive aid and an antiseptic. The rosemary oil comprises from about 0.05 to about 0.15 weight percent of the solid component.

Thyme is present in the solid component of the inventive formulation, acting as an antiseptic agent. The thyme comprises from about 0.05 to about 0.15 weight percent of the solid component.

Bismuth citrate is present in the solid component of the inventive formulation, acting as an agent to sooth the lining of the stomach. The bismuth citrate comprises from about 5 to about 10 weight percent of the solid component.

Grapefruit seed is present in the solid component of the inventive formulation, acting as an antifungal agent. The grapefruit seed comprises from about 2 to about 6 weight percent of the solid component.

The effective daily dosage for the food supplement and herbal intestinal tract cleaner according to the present invention ranges from about 15 drops/day to about 20 drops for the liquid component, about 4800 mg. for the solid component. Preferably, the effective dosage is about 20 drops for the liquid component and about 4800 mg. for the solid component. The food supplement and herbal intestinal tract cleaner according to the present invention is taken orally.

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. An herbal formulation, comprising a liquid and a solid, said liquid comprising:
   black walnut;
   wormwood;
   clove;
   orange peel; and
   marshmallow; and
said solid comprising:
   black walnut;
   wormwood;
   clove;
   quassia;
   pumpkin seed;
   deodorized garlic;
   pippli;
   cascara sagrada;
   calcium undecylenate;
   caprylic acid;
   pau d'arco;
   rosemary oil;
   thyme;
   bismuth citrate; and
   grapefruit seed.

2. The herbal formulation according to claim 1, wherein the concentration of black walnut in the liquid ranges from about 15 to about 25 weight percent.

3. The herbal formulation according to claim 1, wherein the concentration of black walnut in the solid ranges from about 7 to about 15 weight percent.

4. The herbal formulation according to claim 1, wherein the concentration of wormwood in the liquid ranges from about 15 to about 25 weight percent.

5. The herbal formulation according to claim 1, wherein the concentration of wormwood in the solid ranges from about 7 to about 15 weight percent.

6. The herbal formulation according to claim 1, wherein the concentration of clove in the liquid ranges from about 15 to about 25 weight percent.

7. The herbal formulation according to claim 1, wherein the concentration of clove in the solid ranges from about 2 to about 6 weight percent.

8. The herbal formulation according to claim 1, wherein the concentration of orange peel in the liquid ranges from about 15 to about 25 weight percent.

9. The herbal formulation according to claim 1, wherein the concentration of marshmallow in the liquid ranges from about 15 to about 25 weight percent.

10. The herbal formulation according to claim 1, wherein the concentration of quassia in the solid ranges from about 7 to about 15 weight percent.

11. The herbal formulation according to claim 1, wherein the concentration of pumpkin seed in the solid ranges from about 2 to about 6 weight percent.

12. The herbal formulation according to claim 1, wherein the concentration of deodorized garlic in the solid ranges from about 5 to about 10 weight percent.

13. The herbal formulation according to claim 1, wherein the concentration of pippli in the solid ranges from about 1 to about 2 weight percent.

14. The herbal formulation according to claim 1, wherein the concentration of cascara sagrada in the solid ranges from about 5 to about 10 weight percent.

15. The herbal formulation according to claim 1, wherein the concentration of calcium undecylenate in the solid ranges from about 10 to about 20 weight percent.

16. The herbal formulation according to claim 1, wherein the concentration of caprylic acid in the solid ranges from about 5 to about 10 weight percent.

17. The herbal formulation according to claim 1, wherein the concentration of pau d'arco in the solid ranges from about 5 to about 10 weight percent.

18. The herbal formulation according to claim 1, wherein the concentration of rosemary oil in the solid ranges from about 0.05 to about 0.15 weight percent.

19. The herbal formulation according to claim 1, wherein the concentration of thyme in the solid ranges from about 0.05 to about 0.15 weight percent.

20. The herbal formulation according to claim 1, wherein the concentration of bismuth citrate in the solid ranges from about 5 to about 10 weight percent.

21. The herbal formulation according to claim 1, wherein the concentration of grapefruit seed in the solid ranges from about 2 to about 6 weight percent.

22. An herbal formulation, comprising a liquid and a solid, said liquid comprising:

from about 15 to about 25 weight percent black walnut;

from about 15 to about 25 weight percent wormwood;

from about 15 to about 25 weight percent clove;

from about 15 to about 25 weight percent orange peel; and from about 15 to about 25 weight percent marshmallow; and said solid comprising:

from about 7 to about 15 weight percent wormwood;

from about 7 to about 15 weight percent black walnut;

from about 7 to about 15 weight percent quassia;

from about 2 to about 6 weight percent clove;

from about 2 to about 6 weight percent pumpkin seed;

from about 5 to about 10 weight percent deodorized garlic;

from about 1 to about 2 weight percent pippli;

from about 5 to about 10 weight percent cascara sagrada;

from about 0.05 to about 0.15 weight percent rosemary oil;

from about 0.05 to about 0.15 weight percent thyme;

from about 5 to about 10 weight percent bismuth citrate; and from about 2 to about 6 weight percent grapefruit seed.

* * * * *